(12) United States Patent
Wolf et al.

(10) Patent No.: US 11,746,040 B2
(45) Date of Patent: Sep. 5, 2023

(54) CERAMIC GLAZE MIXER CONTROL

(71) Applicants: Andrea Wolf, Issaquah, WA (US); Gabriel Takacs, Issaquah, WA (US)

(72) Inventors: Andrea Wolf, Issaquah, WA (US); Gabriel Takacs, Issaquah, WA (US)

( * ) Notice: Subject to any disclaimer, the term of this patent is extended or adjusted under 35 U.S.C. 154(b) by 1281 days.

(21) Appl. No.: 16/180,944

(22) Filed: Nov. 5, 2018

(65) Prior Publication Data
US 2020/0140321 A1 May 7, 2020

(51) Int. Cl.
| | | |
|---|---|---|
| *C03C 8/14* | (2006.01) | |
| *C03C 8/02* | (2006.01) | |
| *C04B 41/86* | (2006.01) | |
| *B01F 23/50* | (2022.01) | |
| *G16C 20/00* | (2019.01) | |
| *C04B 111/00* | (2006.01) | |
| *B01F 101/30* | (2022.01) | |
| *B01F 35/22* | (2022.01) | |

(52) U.S. Cl.
CPC .............. *C03C 8/14* (2013.01); *B01F 23/511* (2022.01); *B01F 23/59* (2022.01); *C03C 8/02* (2013.01); *C04B 41/86* (2013.01); *G16C 20/00* (2019.02); *B01F 23/56* (2022.01); *B01F 35/2202* (2022.01); *B01F 2101/30* (2022.01); *C03C 2205/00* (2013.01); *C04B 2111/00198* (2013.01)

(58) Field of Classification Search
CPC .. B01F 2101/30; B01F 35/2202; B01F 23/59; B01F 33/844; B01F 33/8442; B01F 33/845; B01F 35/2206; B01F 35/2207
USPC ......................................................... 702/22
See application file for complete search history.

(56) References Cited

U.S. PATENT DOCUMENTS

| | | | | |
|---|---|---|---|---|
| 8,666,540 B2* | 3/2014 | Milhorn | ................. | B01F 29/20 700/239 |
| 2005/0259511 A1* | 11/2005 | Orton | ...................... | B01F 33/86 366/207 |
| 2008/0257446 A1* | 10/2008 | Oakes | ................. | B01F 33/8442 141/94 |
| 2017/0154372 A1* | 6/2017 | Balooch | ................. | B01F 29/10 |
| 2018/0271791 A1* | 9/2018 | Myerson | ................. | B29C 43/34 |

OTHER PUBLICATIONS

"Insight-live.com Instruction manual", Retrieved at <<https://insight-live.com/insight/help/index.html>>, Retrieved on Nov. 1, 2018, pp. 45.
"Glazy.org", Retrieved at <<https://glazy.org/search?base_type=460>>, Retrieved on Nov. 1, 2018, pp. 2.

* cited by examiner

*Primary Examiner* — Marc C Howell
(74) *Attorney, Agent, or Firm* — Stephen T. Neal

(57) ABSTRACT

In one example, a solver engine may execute a reverse calculation to determine a recipe ingredient set based on a goal descriptor describing a ceramic glaze. A descriptor interface of the solver engine may receive a goal descriptor describing a ceramic glaze. A model applicator of the solver engine may apply a glaze process model to the goal descriptor. The model applicator may automatically reverse calculate a glaze recipe describing a recipe ingredient set to produce the ceramic glaze described by the goal descriptor. A glaze mixing machine interface may direct a glaze mixing machine to mix the recipe ingredient set to produce the ceramic glaze.

20 Claims, 13 Drawing Sheets

200

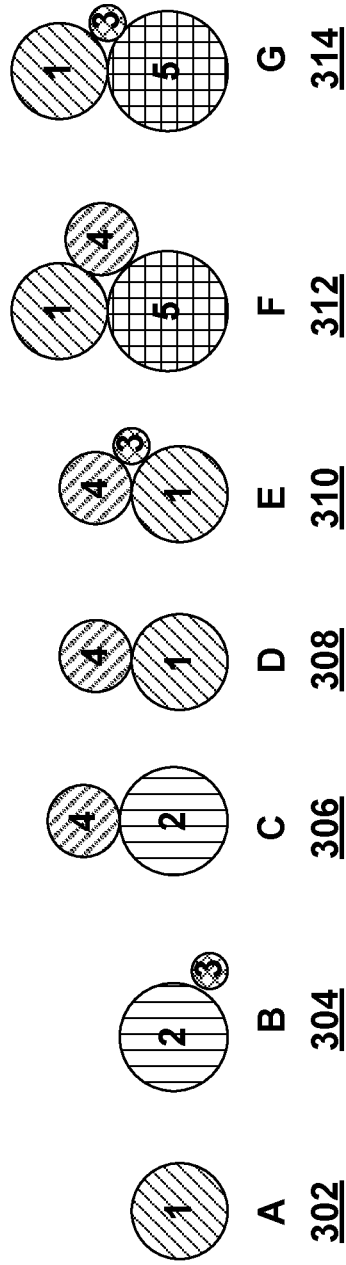

320

*340*

*360*

400

CERAMIC GLAZE MIXER CONTROL

BACKGROUND

To create a ceramic glaze for a piece of pottery, or other objects, a ceramic technician may mix a specified list of ingredients. For example, a simple recipe may list the types and amounts of materials to use, such as twenty percent Custer Feldspar, twenty percent Ferro Frit 3134, twenty percent Wollastonite, twenty percent Edgar Plastic Kaolin, and twenty percent Silica. The ingredients may range from simple oxides to complex, naturally-occurring minerals and materials. The ceramic technician may mix fine powders of these materials with water to form a glaze slurry. The ceramic technician then may apply the glaze slurry to the unglazed clay. The ceramic technician may then place the slurry-coated clay in a kiln, or high-temperature furnace. The kiln may melt and integrate the ingredients of the glaze slurry. The heat of the kiln may transform the chemical nature of the glaze ingredients. In the process of the chemical transformation, the ingredients may volatilize, or emit gasses. The firing process may result in a glaze that contains ceramic-oxides. The physical and aesthetic properties of the glaze may depend on the precise ratios of these oxides.

SUMMARY

This Summary is provided to introduce a selection of concepts in a simplified form that is further described below in the Detailed Description. This Summary is not intended to identify key features or essential features of the claimed subject matter, nor is it intended to be used to limit the scope of the claimed subject matter.

Examples discussed below relate to automatically executing a reverse calculation to determine a recipe ingredient set based on a goal property description or a goal chemical composition. A descriptor interface of a solver engine may receive a goal descriptor describing a ceramic glaze. A model applicator of the solver engine may apply a glaze process model to the goal descriptor. The model applicator may automatically reverse calculate a glaze recipe describing a recipe ingredient set to produce the ceramic glaze described by the goal descriptor. A glaze mixing machine interface may direct a glaze mixing machine to mix the recipe ingredient set to produce the ceramic glaze.

DRAWINGS

To describe the manner in which the above-recited and other advantages and features can be obtained, a more particular description is set forth and will be rendered by reference to specific examples thereof which are illustrated in the appended drawings. Understanding that these drawings depict only typical examples and are not therefore to be considered to be limiting of its scope, implementations will be described and explained with additional specificity and detail through the use of the accompanying drawings.

FIG. 3a illustrates, in a block diagram, one example of a set of ingredients.

DETAILED DESCRIPTION

Figure 1:
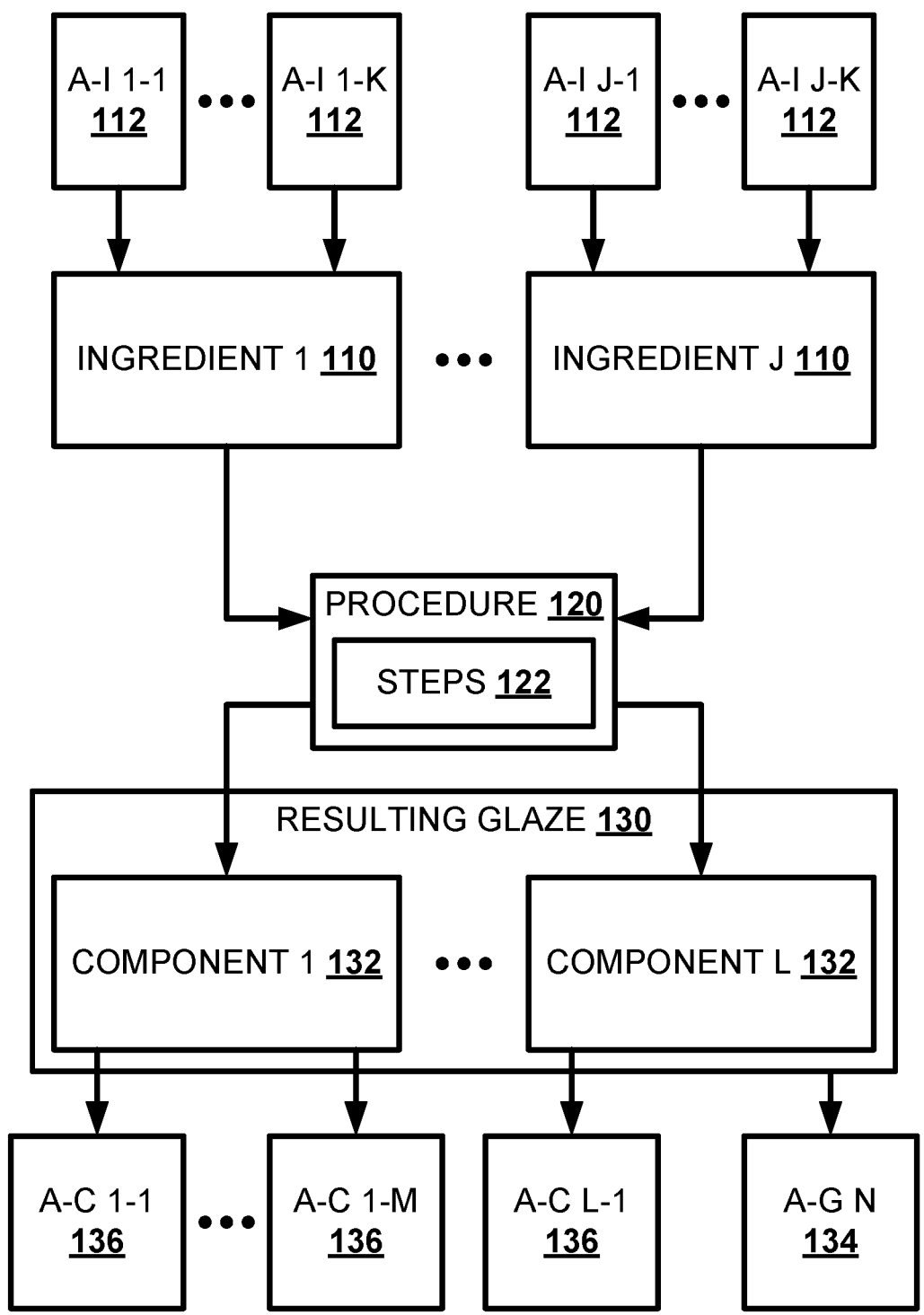
FIG. 1 illustrates, in a block diagram, one example of a glazing process.

Examples are discussed in detail below. While specific implementations are discussed, it should be understood that this is done for illustration purposes only. A person skilled in the relevant art will recognize that other components and configurations may be used without parting from the spirit and scope of the subject matter of this disclosure. The implementations may be a solver engine, a computing device, or a machine-implemented method.

A ceramic technician may separate ceramic oxides into classes based on the ceramic oxides' effect on the resulting glaze. This categorization may not be precise as many oxides participate in multiple effects. At the highest level, a ceramic technician may be concerned with two classes of oxides: base oxides used in the base glaze recipe and coloring oxides that strongly affect the color, opacity, or surface effect. Common and important base oxides may be $Li_2O$, $K_2O$, $Na_2O$, CaO, MgO, BaO, SrO, ZnO, PbO, $Al_2O_3$, $B_2O_3$, $SiO_2$, $P_2O_5$. Common coloring oxides may be $Fe_2O_3$, $TiO_2$, ZrO, SnO, CuO, CoO, MnO, NiO, CrO. A solver engine may list recipes that use raw materials without prohibitively expensive or inconvenient pure oxides.

The ceramic technician may use a molar fraction or a unity molecular formula for ceramic oxides to compare glaze chemistry. A molar fraction may describe the relative number of molecules of each ceramic oxide in a glaze normalized such that the total of the formula sums to one. A unity formula may describe the relative number of molecules of each ceramic oxide in a glaze, normalized such that the total of fluxing oxides sums to one. The characteristics of the finished glaze may be determined primarily by the ratios of the ceramic oxides. Thus, a ceramic technician may perform glaze calculations to compute the unity molecular formula from a recipe, referred to as a forward calculation. Given a chemical assay of each of the raw materials in a recipe, a ceramic technician may compute the unity molecular formula that results from the glaze recipe. Such calculation may be carried out by hand, but microprocessor-based computers may assist in the tedious calculations.

Though the resulting glaze may primarily be defined by the ceramic oxides, many additional properties of the raw materials may contribute to the utility of the glaze slurry. For example, a ceramic technician may seek components in a glaze slurry that are not water-soluble. The ceramic technician may seek components that stay suspended in the water column for a significant duration so that the glaze may be evenly applied. The ceramic technician may seek a glaze with minimal shrinking while drying to avoid cracking. These properties may be controlled by the choice of raw ingredients. Two ingredients which contribute similar oxides may behave very differently in the slurry. The ceramic technician may seek to formulate a glaze recipe that has the desired physical and chemical properties before and after the firing.

FIG. 1 illustrates, in a block diagram, one example of a glazing process 100. The glazing process 100 may have one or more ingredients 110 to be added to the glaze slurry. Water may be included as one of the ingredients 110. Each ingredient 110 may have one or more ingredient attribute 112 describing a characteristic of the ingredient 110. For example, the ingredient attribute 112 may describe a unity molecular formula, flocculation, solubility, loss on ignition, or a monetary cost. As stated previously, a unity molecular formula may describe the ratios of ceramic oxides to each other within the overall mineral. Flocculation may describe a degree to which ingredients suspend in water. Solubility may describe a degree to which an ingredient dissolves in water. Monetary cost may describe the total monetary cost of raw materials used in the recipe. The solver engine may associate the ingredient attributes 112 with the ingredient 110. Thus, the ceramic technician may supply the ingredient attribute 112, with the solver engine determining the appropriate ingredient 110.

The glazing system may execute a procedure 120 on the ingredients. The procedure 120 may have one or more steps 122. These steps 122 may include measuring, mixing, and heating steps. The procedure 120 may have different steps 122 depending on the ingredients 110 used.

The glazing process 100 may produce a resulting glaze 130 having one or more components 132, referring to an element or a compound present in the resulting glaze 130. The resulting glaze 130 may have glaze attributes 134 describing a characteristic of the resulting glaze 130. Further, each component 132 may have one or more component attribute 136 describing a characteristic of the component 132. For example, the glaze attribute 134 or the component attribute 136 may describe a melting point, loss on ignition, hardness, surface texture, or a coefficient of thermal expansion. A melting point may describe the temperature or temperature range at which a component begins to soften from solid to liquid. Loss on ignition may describe a fraction of the mass of the dry glaze that is off-gassed in firing. Hardness may describe the resistance of a component to scratching or deformation. Surface texture may describe the degree to which the surface is glossy, matte, rough, smooth, or crystallized. A coefficient of thermal expansion may describe an amount of expansion of a glaze component 132 as the glaze is heated. The solver engine may associate the component attributes 136 with the component 132. Thus, the ceramic technician may supply the component attribute 136, with the solver engine determining the appropriate component 132.

A solver engine may model the glaze process in a mathematical description to act as a glaze process model. While the solver engine is described herein as being applied to a glaze process, a chemist may use the solver engine to apply any type of mixture process model to any type of mixture. A forward calculation of the glaze process model may allow a ceramic technician to anticipate the results of a glaze recipe. However, the ceramic technician may be unable to derive a recipe to achieve an exact desired result, as defined by the glaze's chemical and physical properties. Typically, a ceramic technician may start with a recipe close to the desired recipe. The ceramic technician may compute the forward calculations to determine the deviation from the desired properties. The ceramic technician may then apply expert knowledge and instinct to adjust the recipe closer to the desired properties. This approach suffers from a few major drawbacks. First, the ceramic technician may have difficulty determining if the desired properties are attainable by any combination of the available raw ingredients. Second, even when an approximate recipe is found, the ceramic technician may be unsure if the best possible recipe has been achieved. Third, the process may be extremely tedious. The primary cause of these problems may be that adjusting any one ingredient in the recipe may simultaneously affect all the chemical and physical properties of the glaze.

To solve this problem, a reverse calculation of the glaze process model may allow a technician to compute a glaze recipe that meets a desired result. While the forward calculation may have a single, well-defined solution, the forward calculation may not allow the technician to directly control the properties of the resulting glaze. Using the reverse calculation, the technician may have control over many more variables and constraints of the inputs and outputs of the glaze process. The solver engine may have two types of inputs to the calculation: a set of goals for each chemical or physical property of the resulting glaze and a set or sets of raw materials, or ingredients, that may be used in the recipe. While experienced ceramic technicians may know specific chemical compositions to achieve specific effects, the solver engine may further abstract the process to allow a ceramic technician to provide attributes of the ingredients or the resulting glaze. The solver engine may then calculate the proper chemical composition of the resulting glaze. The solver engine may output a recipe containing ingredients and amounts, along with an indication of the feasibility of the problem.

A goal may describe a minimum, a target, a maximum, or an importance value. The minimum, the target, and the maximum values may each be described in the units of the property. The importance, or weight, may be described in a unitless value representing the relative importance of that goal in comparison to the other goals. The solver engine may attempt to get the value of the property associated with the goal as close as possible to the target between the minimum and maximum values. In addition to user-provided limits, the solver engine may consider physical constraints, such as non-negativity of oxide amounts or limiting the amount of materials in the base recipe to a fixed, predefined amount.

An ingredient store may represent those ingredients available, though not required, for the recipe. Each material may have an associated set of chemical and physical properties. Multiple ingredient stores may be provided with a priority ordering, with the solver engine executing a calculation for each store in the order provided or independently. The solver engine may terminate upon finding a solution that meets the constraints.

The outputs of the reverse calculation may be the feasibility of the problem and the recipe that comes closest to meeting the constraints or targets. If no feasible solution is available, the solver engine may proceed to the next set of materials or widen the limiting constraint to make the problem feasible. The solver engine may display an optimal recipe for each ingredient store, along with an accuracy score for each recipe.

In one example, a solver engine may execute a reverse calculation to determine a recipe ingredient set based on a goal descriptor. A descriptor interface of the solver engine may receive a goal descriptor describing a ceramic glaze. A model applicator may apply a glaze process model to the goal descriptor. The model applicator may automatically reverse calculate a glaze recipe describing a recipe ingredient set to produce the ceramic glaze described by the goal descriptor. A glaze mixing machine interface may direct a glaze mixing machine to mix the recipe ingredient set to produce the ceramic glaze.

Figure 2:
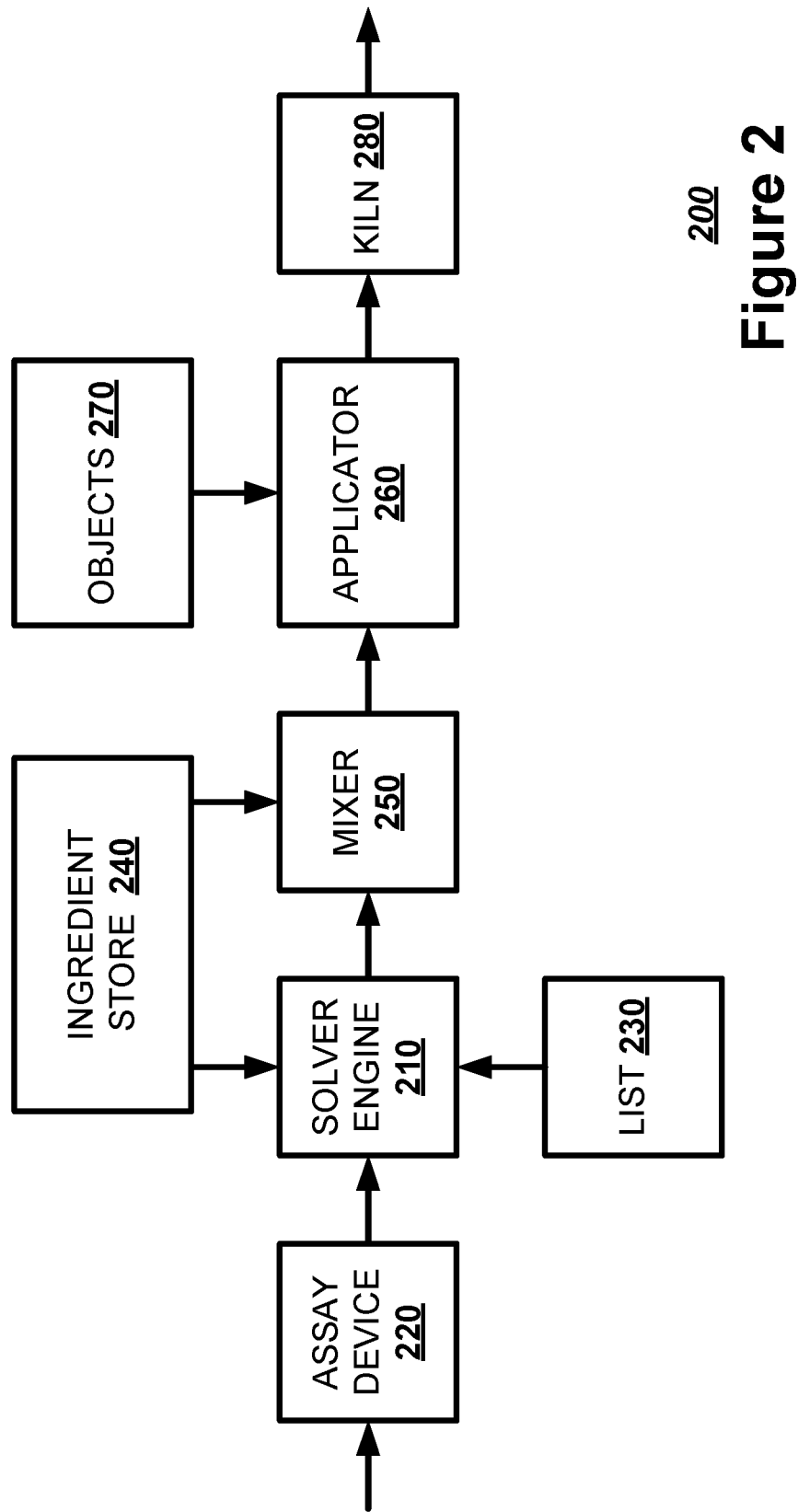
FIG. 2 illustrates, in a block diagram, one example of a glazing system.

FIG. 2 illustrates, in a block diagram, one example of a glazing system 200. The glazing system 200 may have a solver engine 210 to perform a reverse glaze calculation to determine a glaze recipe listing ingredients and steps for producing a glaze based on a set of goal descriptors describing the properties of the resulting glaze desired by the glaze technician. A glaze recipe may include water along with the other ingredients. For example, a goal descriptor may include a unity molecular formula, flocculation, solubility, loss on ignition, a coefficient of thermal expansion, a monetary cost, and associated limits and importance values. The glazing system 200 may produce a glaze recipe, a mixed glaze powder, a glaze slurry, an unfired, glazed object, or a fired, glazed object based on the ingredients on hand. An object may be a test tile, a piece of pottery, a piece of metal or other object.

An assay device 220 may analyze an example glaze sample to provide a list of goal descriptors to the solver engine 210. The assay device 220 may use spectrometry or other chemical or physical analysis methods to determine the properties of the example glaze piece. Examples of such analysis methods may include, but are not limited to, hardness testing, thermogravimetric analysis, dilatometry, tensiometry, and viscometry. The solver engine 210 may receive a parameter list 230 from a ceramic technician describing further goal descriptors for the resulting glaze.

The solver engine 210 may receive an available ingredient list from a recipe ingredient store 240. The recipe ingredient store 240 is the set of available recipe ingredients. The solver engine 210 may factor the available ingredient list into the reverse glaze calculation. The solver engine 210 may also receive a parameter list 230 describing ingredient descriptors for ingredients desired by the ceramic technician. The solver engine 210 may provide the glaze recipe to a glaze mixing machine 250 to mix the glaze. The recipe ingredient store 240 may provide the listed recipe ingredient set to the glaze mixing machine 250. The glaze mixing machine 250 may mix the recipe ingredient set in either a batch mixing process or continuous mixing process to produce the glaze slurry.

The glaze mixing machine 250 may send the glaze slurry to a glaze application device 260. The glaze application device 260 may receive one or more blank objects 270. The one or more blank objects may be a test tile, a piece of pottery, a piece of metal or other objects. The glaze application device 260 may apply the glaze slurry to the one or more blank objects 270. The glaze application device 260 may provide the glazed objects to a kiln 280 for firing. The kiln 280 may fire the glazed objects to provide finished objects.

In some instances, the glazing system may be physically incapable of creating a resulting glaze mixture that exactly matches the goal descriptor based on the available ingredients, illustratable by comparison to placing different size and types of balls in a bucket. As working with pure elements as ingredients may be prohibitively expensive, adding one ingredient to add an element to the final glaze may necessarily add a different element that has different chemical properties. FIGS. 3a-d illustrate, in block diagrams, alternate examples of a mixture process to demonstrate the "Balls in a Bucket" issue. The "Balls" represent different atoms in the molecules of ingredients to be added to a mixture. Each atom may have a different atomic mass based on the atom type. For example, Hydrogen may have an atomic mass of 1 atomic unit, representing one proton. Meanwhile, oxygen may have an atomic mass 15.99 atomic units, representing eight protons and a range around eight neutrons. The "Bucket" refers to a representative portion of the mixture. To achieve a desired mixture having a specific atomic makeup, the mixer may add specific ingredients in specific amounts. An issue may arise when the available ingredients are mathematically incapable of providing the desired amount of elements for the desired mixture.

FIG. 3a illustrates, in a block diagram, one example of a set 300 of ingredient molecules. While certain element configurations for molecules are provided as examples, these molecules do not represent ingredients used in creating a glaze slurry or even substances that occur in nature. For example, Molecule A 302 may have a single medium sized atom of Element 1, such as oxygen. Molecule B 304 may have a large sized atom of Element 2, such as iron, and a small sized atom of Element 3, such as hydrogen. Molecule C 306 may have a large sized atom of Element 2, such as iron, and a medium sized atom of Element 4, such as carbon. Molecule D 308 may have a medium sized atom of Element 1, such as oxygen, and a medium sized atom of Element 4, such as carbon. Molecule E 310 may have a medium sized atom of Element 1, such as oxygen; a medium sized atom of Element 4, such as carbon; and a small sized atom of Element 3, such as hydrogen. Molecule F 312 may have a large sized atom of Element 5, such as platinum; a medium sized atom of Element 1, such as oxygen; and a medium sized atom of Element 4, such as carbon. Molecule G 314 may have a large sized atom of Element 5, such as platinum; a medium sized atom of Element 1, such as oxygen; and a small sized atom of Element 3, such as hydrogen.

Figure 3B:
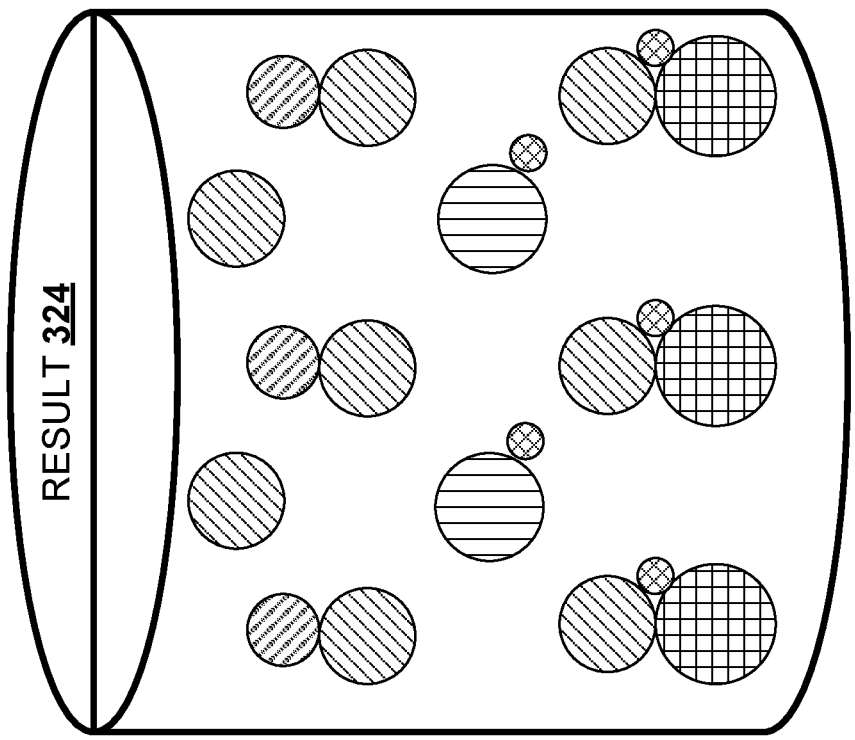
FIG. 3b illustrates, in a block diagram, one example of an efficient mixture of ingredients.
Figure 3B:
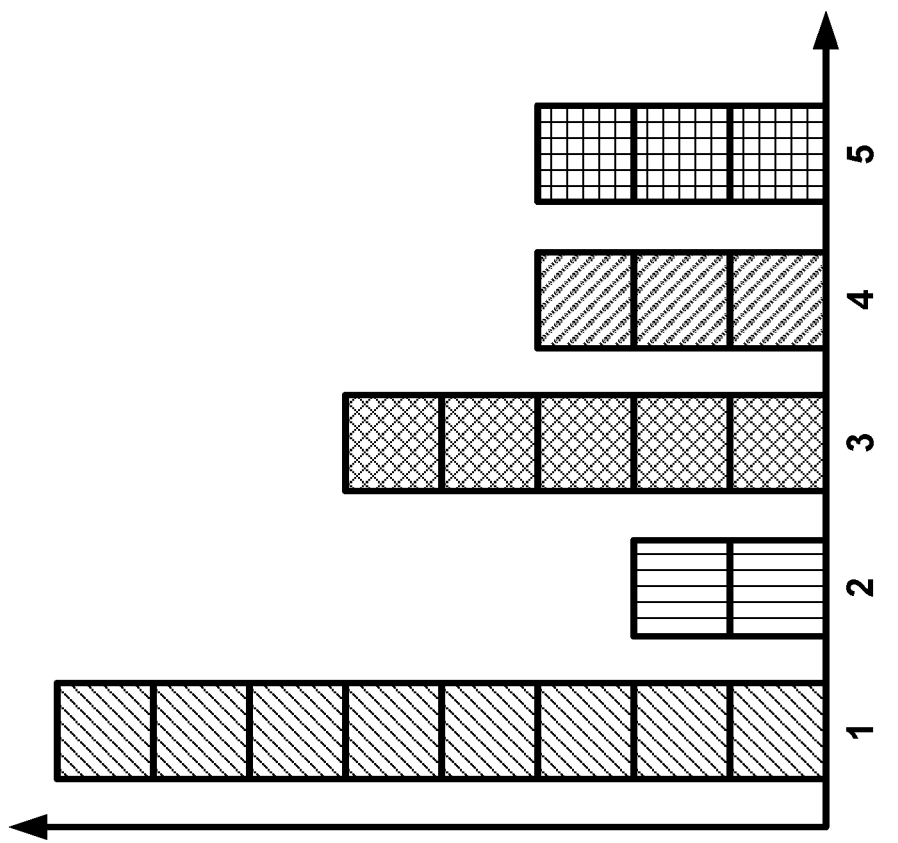

FIG. 3b illustrates, in a block diagram, one example of an efficient mixture 320 of ingredients. The solver engine may have a goal descriptor set 322 describing elements for a goal resulting mixture. An efficient mixture 320 has a mixture result 324 that meets each goal descriptor of the goal descriptor set 322. The goal descriptor set 322 may list eight parts of Element 1, two parts of Element 2, five parts of Element 3, three parts of Element 4, and three parts of Element 5. The mixture result 324 may have three parts Molecule G 314, two parts Molecule B 304, three parts Molecule D 308, and two parts Molecule A 302.

Figure 3C:
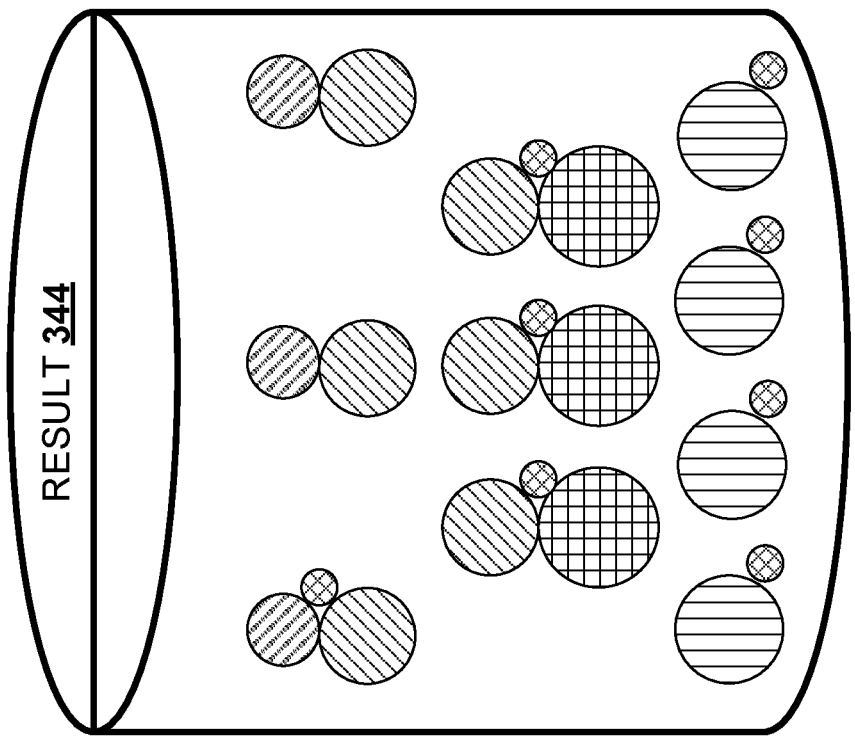
FIG. 3c illustrates, in a block diagram, one example of an inefficient mixture of ingredients.
Figure 3C:
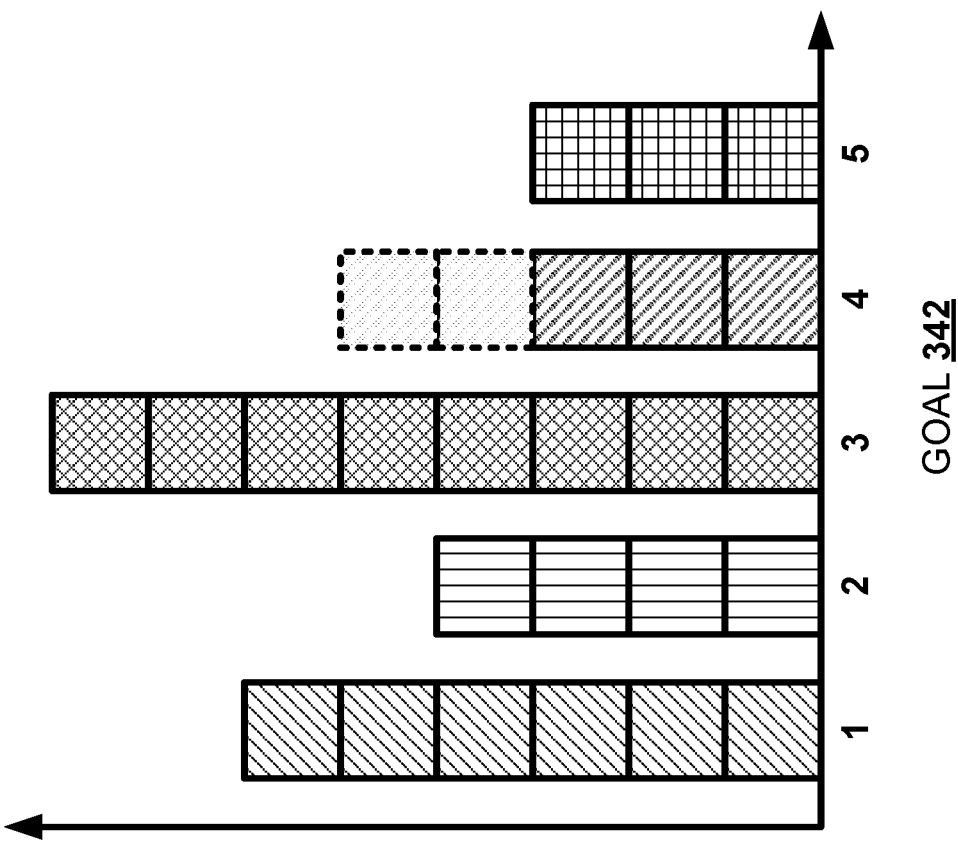

FIG. 3c illustrates, in a block diagram, one example of an inefficient mixture 340 of ingredients. The solver engine may have a goal descriptor set 342 describing elements for a goal resulting mixture. An inefficient mixture 340 has a mixture result 344 that fails to meet each goal descriptor of the goal descriptor set 342. The goal descriptor set 342 may list six parts of Element 1, four parts of Element 2, eight parts of Element 3, five parts of Element 4, and three parts of Element 5. The mixture result 344 may have four parts Molecule B 304, three parts Molecule G 314, one part Molecule E 310, and two parts Molecule D 308. In this inefficient mixture 340, the goal descriptor for Element 4 is two parts short of having five parts Element 4. Thus, the mixture result 344 may have different properties than the goal resulting mixture.

Figure 3D:
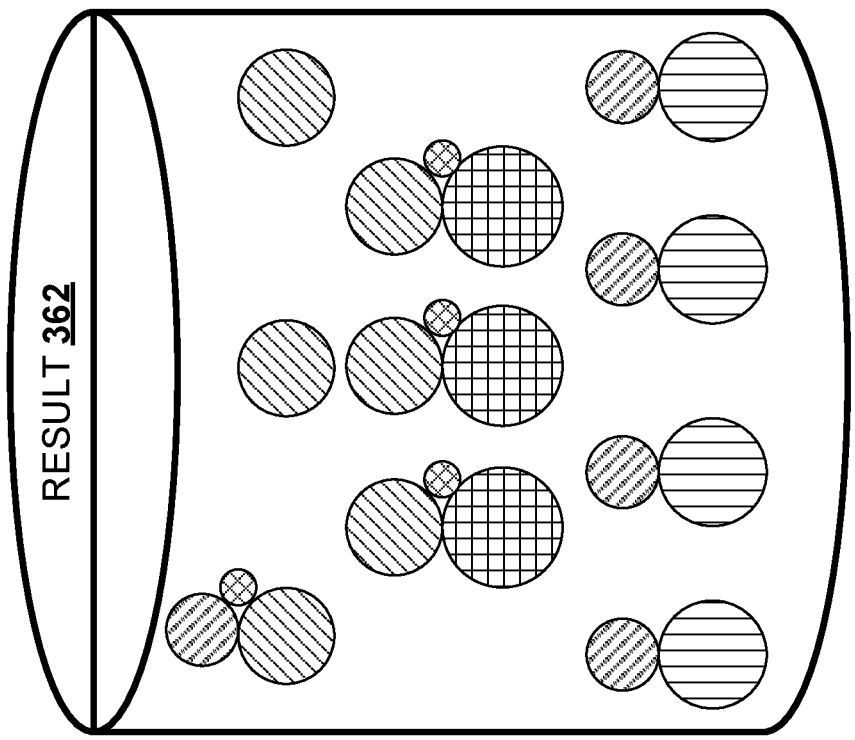
FIG. 3d illustrates, in a block diagram, one example of an alternate inefficient mixture of ingredients.
Figure 3D:
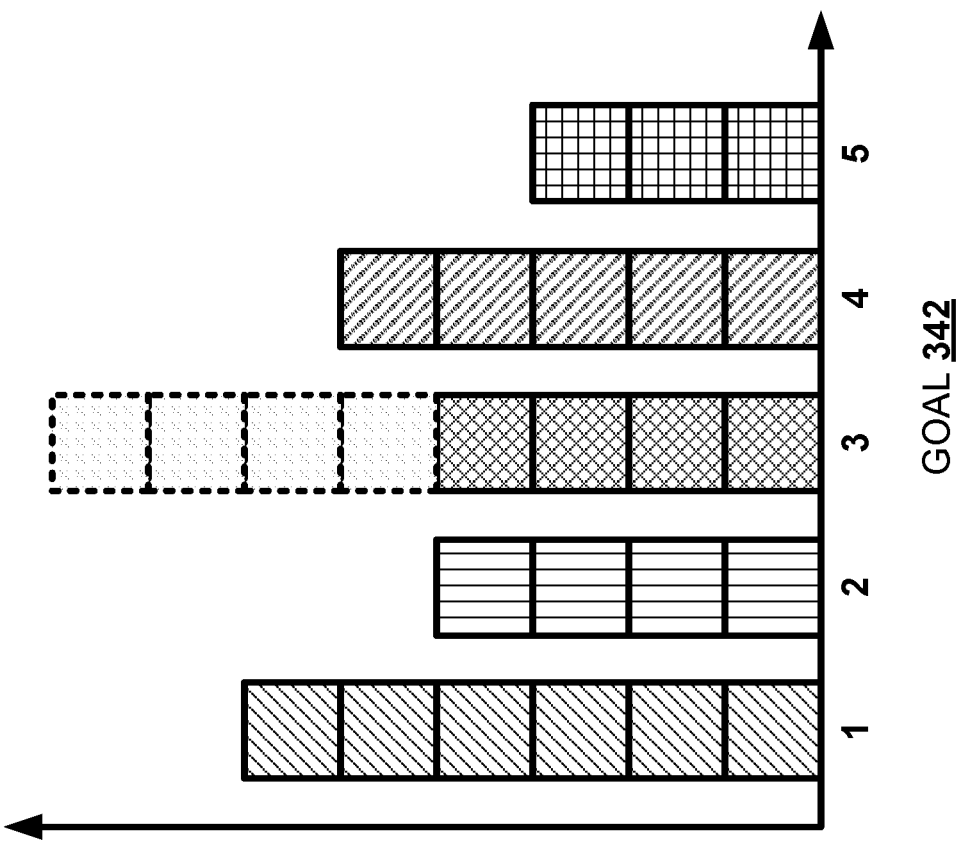

FIG. 3d illustrates, in a block diagram, one example of an alternate inefficient mixture 360 of ingredients. The solver engine may have the same goal descriptor set 342 describing elements for a goal resulting mixture. The alternate inefficient mixture 360 has a mixture result 362 that fails to meet each goal descriptor of the goal descriptor set 342 in a different manner than the other mixture result 344. The goal descriptor set 342 may list six parts of Element 3, four parts of Element 2, eight parts of Element 3, five parts of Element 4, and three parts of Element 5. The mixture result 362 may have four parts Molecule C 306, three parts Molecule G 314, one part Molecule E 310, and two parts Molecule A 302. In this example, the goal descriptor for Element 3 is four parts short of having eight parts Element 3. Thus, the mixture result 362 may have different properties than the goal resulting mixture and the other mixture result 344.

Figure 4:
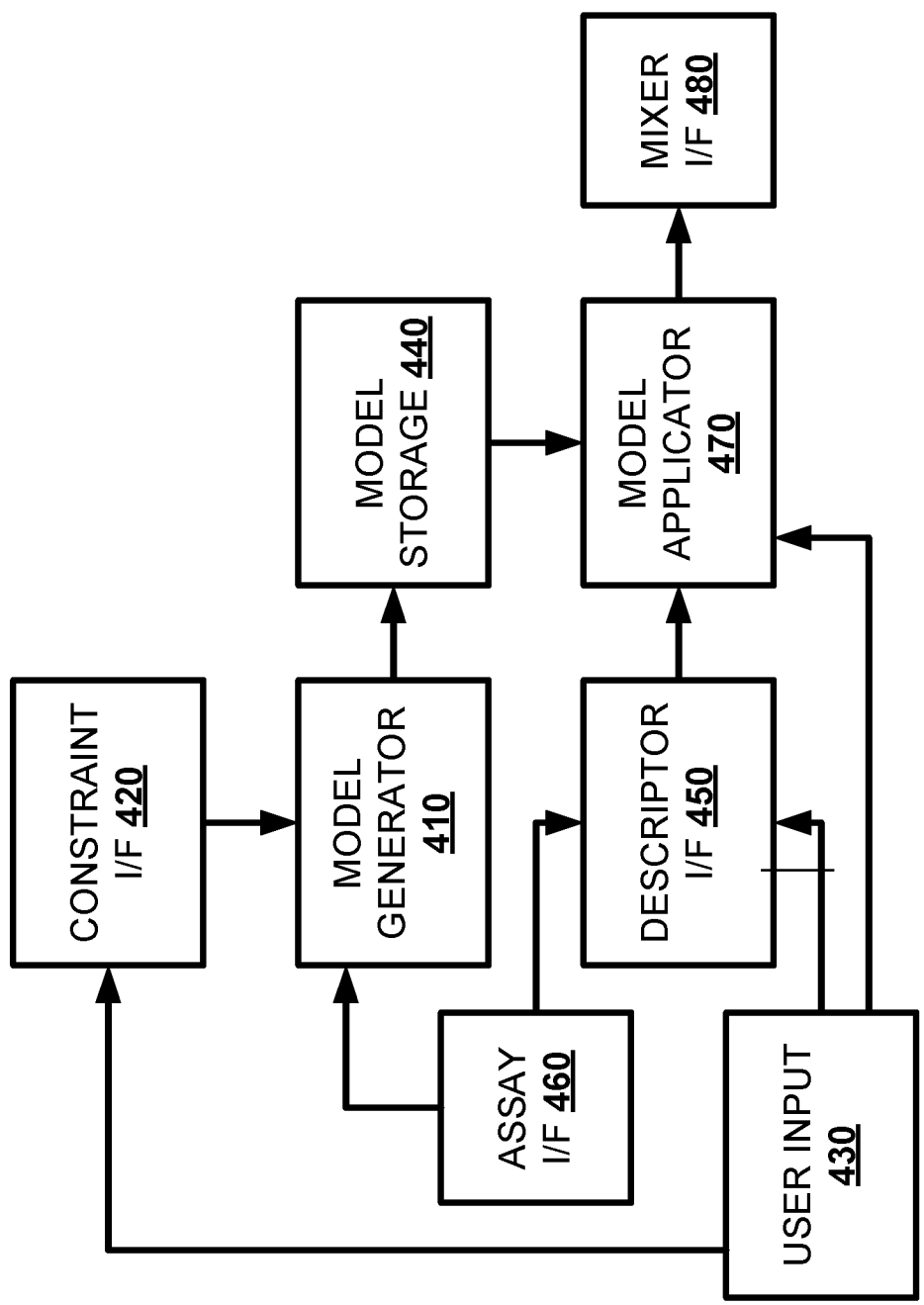
FIG. 4 illustrates, in a block diagram, one example of a solver engine.

FIG. 4 illustrates, in a block diagram, one example of a solver engine 400. The solver engine 400 may have a model generator 410 to generate a mathematical description of a glazing process to act as a glaze process model. The glaze process model may represent an ordered list of materials, referred to as the material database, with a vector, M, having a length m. The glaze process model may represent a recipe with a vector, r, of length m, with $r_i$ representing the amount of the i-th material in the material database. The glaze process model may define the forward calculation as y=f(r, M), where y is a vector of n values describing the result of the glazing process. By inputting a goal result for the vector y, the solver engine may solve for the input material described in recipe vector r. The j-th element of y represents a physical or chemical property associated with the j-th goal, g. A goal may be represented by a set of four values, such as a minimum value, a target value, a maximum value, and an importance value. The model generator 410 may define these values as $g_j^{min}$, $g_j^{tgt}$, $g_j^{max}$, $g_j^{imp}$, respectively.

The model generator 410 may define a cost for a recipe as compared to a set of goals, such that minimizing the cost may yield an optimal recipe. The model generator 410 may define the cost function, c(y), as a weighted sum of squared errors, $$c(y)=\Sigma_{j=1}^n g_j^{imp}(y_j-g_j^{tgt})^2.$$

Using this cost function, the model generator 410 may introduce a constrained optimization problem to factor a minimum value and a maximum value of the goals, as well as the constraints of a recipe that must sum to one.

The model generator 410 may minimize a cost function c with respect to the input parameter over r $$c(f(r;M))$$

While minimizing this cost function, the model generator 410 may constrain the glaze calculation to $$1=\Sigma_{i=1}^m=r_i,$$

$$0 \leq r_i \leq 1, \forall i=1 \ldots m,$$

$$g_j^{min} \leq y_j \leq g_j^{max}, \forall j=1 \ldots n$$

Note that the forward calculation, f(r,M), is a convex function of the input r, for a fixed value of M. The above optimization problem has a quadratic cost function, and linear and inequality constraints. Therefore, the overall optimization is a convex problem and a globally optimal solution may be efficiently computed.

A constraint interface 420 may receive a set of user constraints describing limitations and rankings for an ingredient or a material in the resulting glaze from a ceramic technician via a user input 430. The user constraints may describe limitations to be placed on the ingredients and the resulting glaze. For example, the user input 430 may be configured to receive an ingredient range for a recipe ingredient of the recipe ingredient set. The ingredient range may be constrained by the amount of material available in an ingredient store or to facilitate a step in the glazing process. Alternately, the user input 430 may be configured to receive an output range for a component material or characteristic of the ceramic glaze. The output range may be constrained to keep a resulting material under a specific amount, such as for toxicity purposes, or to guarantee that a specific amount of a material is present in the final product. The user input 430 may receive a goal property weight for a goal property description of the ceramic glaze. The user input 430 may receive an ingredient property weight for a recipe ingredient of the recipe ingredient set. The model generator 410 may generate a glaze process model based on the set of user constraints. If no user constraints have been received, the model generator 410 may use a set of default values. The model generator 410 may set a goal property range for a goal property description of the ceramic glaze. The model generator 410 may set an ingredient property range for a recipe ingredient of the recipe ingredient set. The model generator 410 may store the glaze process model in a model storage 440.

A descriptor interface 450 may receive a set of goal descriptors describing a ceramic glaze using a set of target values. An assay device interface 460 may receive from an assay device a scan of a glaze sample to determine a goal chemical composition to act as a goal descriptor for the ceramic glaze. The assay device 460 may provide to the descriptor interface 450 the resulting goal descriptor. Further, the user input 430 may receive a goal chemical composition to act as the goal descriptor for the ceramic glaze. Alternately, the user input 430 may receive a goal property description to act as the goal descriptor for the ceramic glaze. Additionally, the user input 430 may receive an ingredient property description for a recipe ingredient of the recipe ingredient set. The descriptor interface 450 may receive a set of target values describing materials or properties of the recipe ingredient set or the resulting glaze from a user input 430. The descriptor interface 450 may provide the set of target values to a model applicator 470. If no goal descriptors have been received, the model applicator 470 may use a set of default target values.

The model applicator 470 may retrieve a glaze process model from the model storage 440. The model applicator 470 may determine the goal chemical composition for the ceramic glaze based on a goal property description. The model applicator 470 may use the glaze process model and the set of target values to perform a reverse calculation to solve for a glaze recipe. The model applicator 470 may apply a glaze process model to a goal descriptor. The model applicator 470 may automatically reverse calculate a glaze recipe describing a recipe ingredient set to produce the ceramic glaze described by the goal descriptor. The model applicator 470 may apply a goal property weight to a goal property description of the ceramic glaze. The model applicator 470 may apply an ingredient property weight to a recipe ingredient of the recipe ingredient set.

The model applicator 470 may solve the optimization problem in two phases. In the first phase, the model applicator 470 may solve a related convex optimization problem to determine if any feasible recipe meets each of the constraints. If the first phase fails to find a solution, the model applicator 470 may mark the goals as unachievable. The model applicator 470 may then return the recipe that is as close as possible to meeting the constraints. In this case, the model applicator 470 may automatically, or through user interaction, expand the unattained constraints to make a recipe feasible. This expansion may occur up to a limit where the maximum and minimum are enforced by the laws of physics, and not ceramic technician preference. In addition to limit expansion, the model applicator may repeatedly increase the set of available materials, M, and re-run the expanded first phase calculation until a solution is found or the available sets of materials is exhausted.

A ceramic technician may already have a recipe that yields a desirable glaze. The ceramic technician may remove or substitute one or more materials in the recipe. The solver engine 400 may automatically generate goals for the reverse calculations by using the forward calculations and settings describing the ceramic technician's preference for tolerances to produce similar outputs to the established recipe. A user input 430 may receive a chemical component adjustment to a chemical component of the goal chemical composition of the ceramic glaze. The model applicator 470 may adjust a complementary chemical component of a goal chemical composition of the ceramic glaze in response to a chemical component adjustment of a chemical component of the goal chemical composition of the ceramic glaze. A complementary chemical component has a characteristic that may be affected by change to the presence or amount of the initial chemical component.

A ceramic technician may seek to retain many or most of the properties of a glaze for a given recipe but alter a few other properties with minimal perturbation to the existing desirable properties. For example, the glaze may not suspend well in water, causing mixing and application problems. In this case, the recipe may match the goals as closely as possible to the existing recipe, but with increased flocculation. In another example, the ceramic technician may wish to increase or decrease the coefficient of thermal expansion of the resulting glaze while matching the goals as closely as possible. In many cases, the ceramic technician may adjust multiple properties of the glaze. These types of operations may be done with or without allowing for changes to the set of materials in the recipe. Further, a glaze may be fine-tuned after mixing and test-firing the glaze to be adjusted. The ceramic technician may nudge the physical or chemical properties to move the glaze towards a desired effect.

The model applicator 470 may then send the recipe to a glaze mixing machine interface 480. The glaze mixing machine interface 480 may direct a glaze mixing machine to mix the recipe ingredient set to produce the ceramic glaze. The assay device interface 460 may receive from an assay device a scan of a resulting ceramic glaze of the glaze recipe. The model applicator 470 may adjust the glaze recipe in response to a scan of a resulting ceramic glaze of the glaze recipe.

Figure 5:
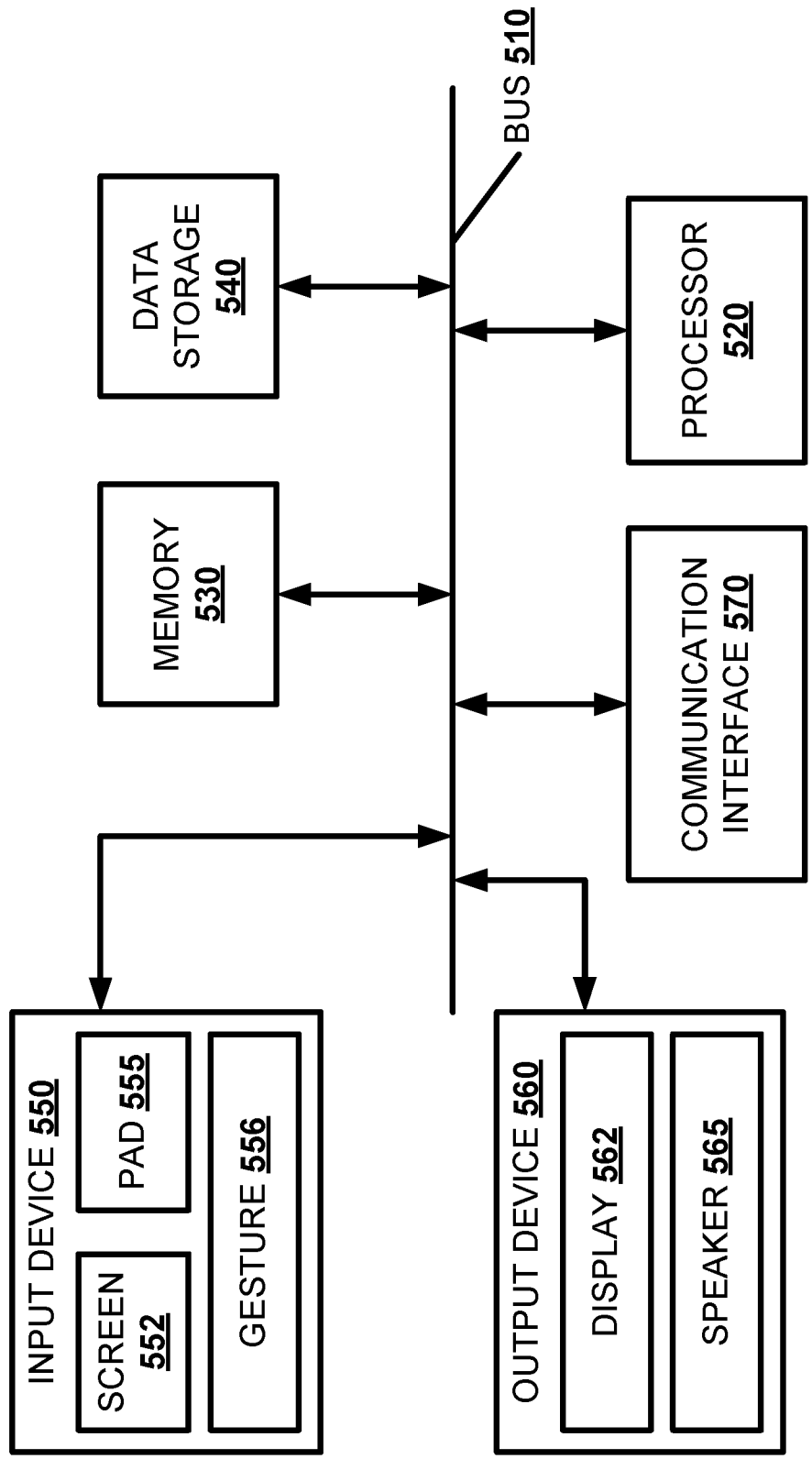
FIG. 5 illustrates, in a block diagram, one example of a computing device.

FIG. 5 illustrates a block diagram of an exemplary computing device 500 which may act as a solver engine. The computing device 500 may combine one or more of hardware, software, firmware, and system-on-a-chip technology to implement the solver engine. The computing device 500 may include a bus 510, a processor 520, a memory 530, a data storage 540, an input device 550, an output device 560, and a communication interface 570. The bus 510, or other component interconnection, may permit communication among the components of the computing device 500.

The processor 520 may include at least one conventional processor or microprocessor that interprets and executes a set of instructions. The processor 520 may act as a model generator to generate a mathematical description of a glazing process to act as a glaze process model. The processor 520 may act as a model applicator to use the glaze process model and the set of target values to perform a reverse calculation to solve for a glaze recipe.

The memory 530 may be a random access memory (RAM) or another type of dynamic data storage that stores information and instructions for execution by the processor 520. The memory 530 may also store temporary variables or other intermediate information used during execution of instructions by the processor 520. The data storage 540 may include a conventional ROM device or another type of static data storage that stores static information and instructions for the processor 520. The data storage 540 may include any type of tangible machine-readable medium, such as, for example, magnetic or optical recording media, such as a digital video disk, and its corresponding drive. A tangible machine-readable medium is a physical medium storing machine-readable code or instructions, as opposed to a signal. Having instructions stored on computer-readable media as described herein is distinguishable from having instructions propagated or transmitted, as the propagation transfers the instructions, versus stores the instructions such as can occur with a computer-readable medium having instructions stored thereon. Therefore, unless otherwise noted, references to computer-readable media/medium having instructions stored thereon, in this or an analogous form, references tangible media on which data may be stored or retained. The data storage 540 may store a set of instructions detailing a method that when executed by one or more processors cause the one or more processors to perform the method. The data storage 540 may also be a database or a database interface for storing an ingredient store. The memory 530 or data storage 540 may act as a model storage to store a glaze process model.

The input device 550 may include one or more conventional mechanisms that permit a ceramic technician to input information to the computing device 500, such as a keyboard, a mouse, a voice recognition device, a microphone, a headset, a touch screen 552, a touch pad 554, a gesture recognition device 556, etc. The input device 550 may act as a descriptor interface configured to receive a goal descriptor describing a ceramic glaze. The input device 550 may act as a user input to receive user constraints or goal descriptors. The input device 550 may act as an assay device interface configured to receive from an assay device a scan of a glaze sample to determine a goal chemical composition to act as a goal descriptor for the ceramic glaze.

The output device 560 may include one or more conventional mechanisms that output information to the ceramic technician, including a display screen 562, a printer, one or more speakers 564, a headset, a vibrator, or a medium, such as a memory, or a magnetic or optical disk and a corresponding disk drive. The output device 560 may be a display screen 562 to present a graphical user interface to a ceramic technician. The display screen 562 may present the glaze recipe describing the recipe ingredient set to produce the ceramic glaze to a ceramic technician. The output device 560 may act as a glaze mixing machine interface configured to direct a glaze mixing machine to mix the recipe ingredient set to produce the ceramic glaze.

The communication interface 570 may include any transceiver-like mechanism that enables computing device 500 to communicate with other devices or networks. The communication interface 570 may include a network interface or a transceiver interface. The communication interface 570 may be a wireless, wired, or optical interface. The communication interface 570 may act as an assay device interface configured to receive from an assay device a scan of a glaze sample, either fired or unfired, to determine a goal chemical composition to act as a goal descriptor for the ceramic glaze. The communication interface 570 may act as a descriptor interface configured to receive a goal descriptor describing a ceramic glaze. The communication interface 570 may send the glaze recipe describing the recipe ingredient set to produce the ceramic glaze to a ceramic technician for presentation. The communication interface 570 may act as a glaze mixing machine interface configured to direct a glaze mixing machine to mix the recipe ingredient set to produce the ceramic glaze.

The computing device 500 may perform such functions in response to processor 520 executing sequences of instructions contained in a computer-readable medium, such as, for example, the memory 530, a magnetic disk, or an optical disk. Such instructions may be read into the memory 530 from another computer-readable medium, such as the data storage 540, or from a separate device via the communication interface 560.

Figure 6:
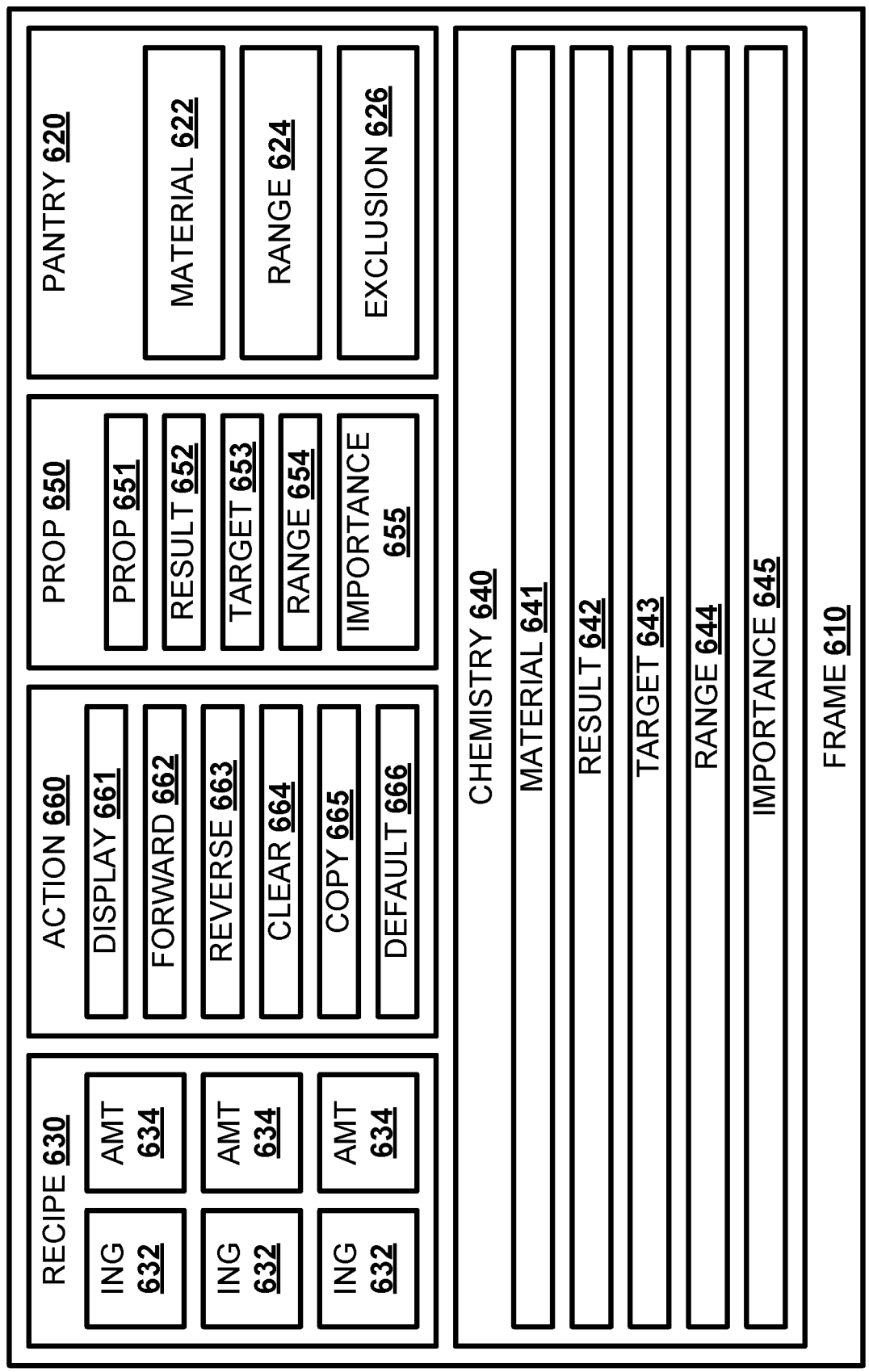
FIG. 6 illustrates, in a block diagram, one example of a user interface for the solver engine.

The user input may provide a user interface to a ceramic technician to allow the ceramic technician to set goals and constraints for the glaze recipe. FIG. 6 illustrates, in a block diagram, one example of a user interface 600 for the solver engine. The user input may display a user interface 600 in a graphic user interface frame 610. The graphic user interface frame 610 may display a pantry panel 620 listing ingredients available for use by the solver engine. The pantry panel 620 may present one or more material listings 622 describing ingredients available in the ingredient store. The pantry panel 620 may associate the material listing 622 with an available range control 624 describing a maximum and a minimum for the ingredients to be included in the recipe. The pantry panel 620 may associate the material listing 622 with an exclusion checkbox 624, allowing the ceramic technician to indicate that an ingredient is to be excluded from the recipe.

The graphic user interface frame 610 may have a recipe panel 630 presenting a set of one or more ingredient listings 632 describing ingredients to make a glaze slurry. The recipe panel 630 may associate an ingredient listing 632 with an amount value 634 representing the amount of an ingredient to mix into the glaze slurry. A ceramic technician may input the ingredients and amount values into the recipe panel 630. Alternately, the solver engine may perform a reverse glaze calculation to solve for the ingredient and amount values and present the results in the recipe panel 630.

The graphic user interface frame 610 may have a chemical panel 640 presenting a set of one or more material listings 641 describing a chemical compound or an element present in a resulting glaze. The chemical panel 640 may associate a material listing 641 with a result value 642 representing the amount of a chemical compound or element present in a resulting glaze. The chemical panel 640 may associate a material listing 641 with a target value 643 representing the goal amount of a chemical compound or element a ceramic technician seeks to produce in a resulting glaze. The chemical panel 640 may associate a material listing 641 with a set of range values 644 representing a maximum and a minimum of a chemical compound or element a ceramic technician seeks to produce in a resulting glaze. The chemical panel 640 may associate a material listing 641 with an importance value 645 representing the importance to the ceramic technician that a chemical compound or element a ceramic technician seeks to produce in a resulting glaze is close to the goal amount. A ceramic technician may input the material listing 641, target value 643, a range value 644, or an importance value 645 into the chemical panel 640. The solver engine may perform a forward glaze calculation to solve for the result values 642 and present the result values 642 in the chemical panel 640.

The graphic user interface frame 610 may have a property panel 650 presenting a set of one or more property listings 651 describing a property of an ingredient in the glaze slurry or a property of a resulting glaze. For example, a property may be loss on ignition, coefficient of thermal expansion, flocculation, solubility, melting point, surface tension, viscosity, or monetary cost of an ingredient per unit weight. The property panel 650 may associate a property listing 651 with a result value 652 describing the resulting property in a resulting glaze. The property panel 650 may associate a property listing 651 with a target value 653 describing the goal property in a resulting glaze. The property panel 650 may associate a material listing 641 with a set of range values 654 representing a maximum and a minimum of a property value describing a resulting glaze. The property panel 650 may associate a property listing 651 with an importance value 655 representing the importance to the ceramic technician that a property in a resulting glaze is close to the goal amount. A ceramic technician may input the property listing 651, target value 653, a range value 654, or an importance value 655 into the property panel. The solver engine may perform a forward glaze calculation to solve for the result values 652 and present the result values 652 in the property panel 650.

The graphic user interface frame 610 may have an action panel 660 presenting a set of one or more buttons to direct the solver engine to perform a set of one or more actions. The action panel 660 may have a display button 661 to direct the solver engine to display the current goal settings to the ceramic technician. The action panel 660 may have forward glazing calculation button 662 to apply the forward glazing calculation to the recipe listing in the recipe panel 630 to generate a result value for the chemical panel 640 and the property panel 650. The action panel 660 may have reverse glazing calculation button 663 to apply the reverse glazing calculation to the goals and constraints entered into the chemical panel 640 and the property panel 650 to generate a recipe listing for the recipe panel 630. The action panel 660 may have a clear button 664 to clear the values entered in to the recipe panel 630, the chemistry panel 640, and the property panel 650. The action panel 660 may have a copy button 665 to copy the values entered in to the recipe panel 630, the chemistry panel 640, or the property panel 650. The action panel 660 may have a fill default button 666 to fill default values into the recipe panel 630, the chemistry panel 640, or the property panel 650.

Figure 7:
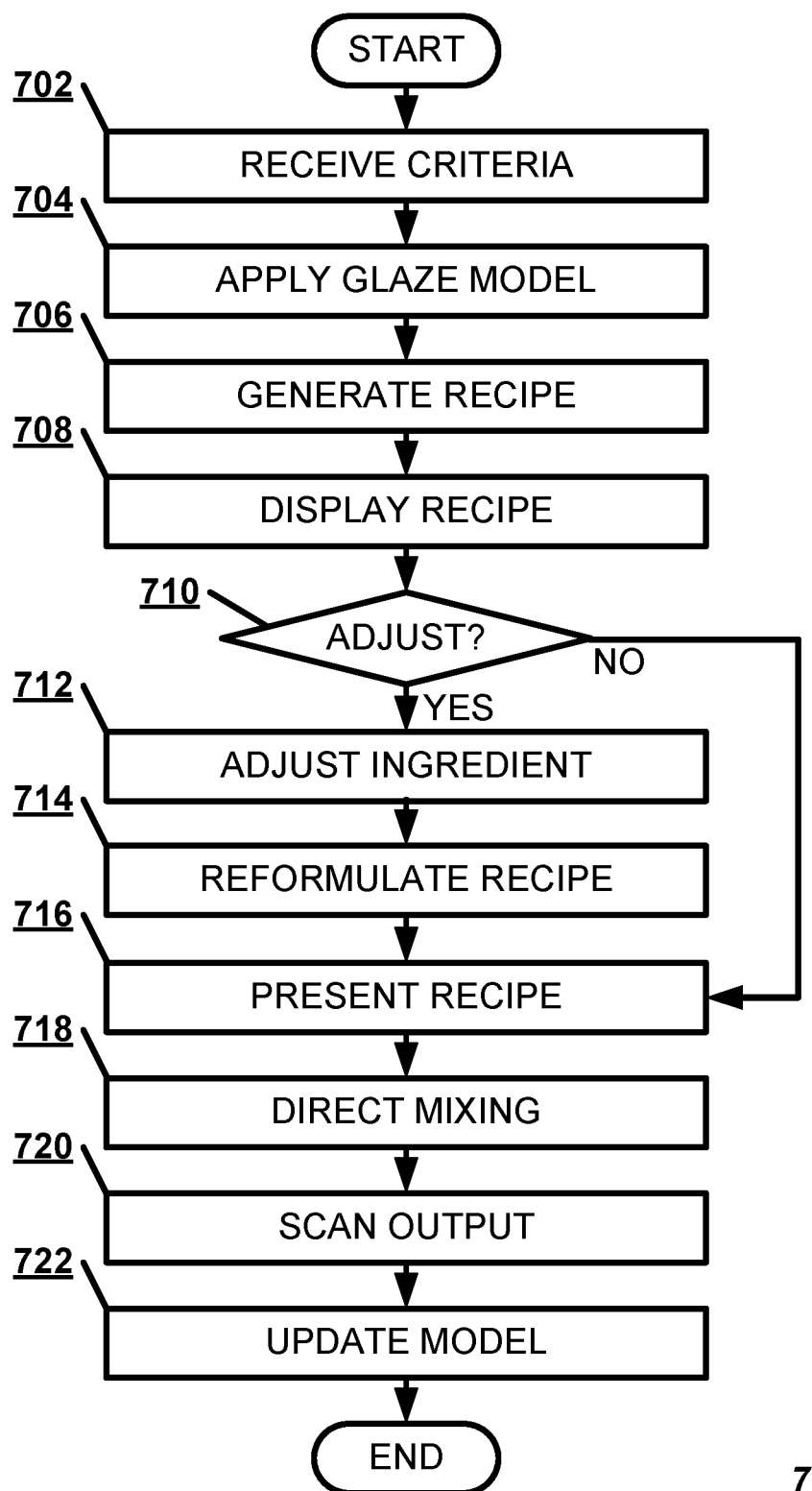
FIG. 7 illustrates, in a flowchart, one example of a method for producing a glaze.

FIG. 7 illustrates, in a flowchart, one example of a method 700 for producing a glaze. The solver engine may receive from a ceramic technician one or more criteria describing an ingredient descriptor describing ingredients for a glaze slurry or a goal descriptor describing a finished glaze (Block 702). The solver engine may apply a glaze process model to a goal chemical composition for a ceramic glaze to determine a resulting chemical composition from a subset of a recipe ingredient store (Block 704). The solver engine may generate a glaze recipe describing a recipe ingredient set to produce the ceramic glaze output having a model chemical composition (Block 706).

The solver engine may display the glaze recipe to a ceramic technician (Block 708). If the solver engine receives from the ceramic technician a chemical component adjustment to a chemical component of the model chemical composition of the ceramic glaze (Block 710), the solver engine may adjust a complementary chemical component of the chemical composition of the ceramic glaze in response to a chemical component adjustment of a chemical component of the model chemical composition of the ceramic glaze output (Block 712). The solver engine may reformulate the glaze recipe to have an updated model chemical composition (Block 714).

A display may present the glaze recipe describing the recipe ingredient set to produce the ceramic glaze to a ceramic technician (716). The solver engine may direct a glaze mixing machine to mix the recipe ingredient set according to the glaze recipe to produce the ceramic glaze from the recipe ingredient set (Block 718). An assay device may scan a resulting glaze sample of the ceramic glaze, either fired or unfired, to determine a resulting chemical composition or other properties for the ceramic glaze (Block 720). The solver engine may update the glaze process model in response to the ceramic glaze (Block 722).

Figure 8:
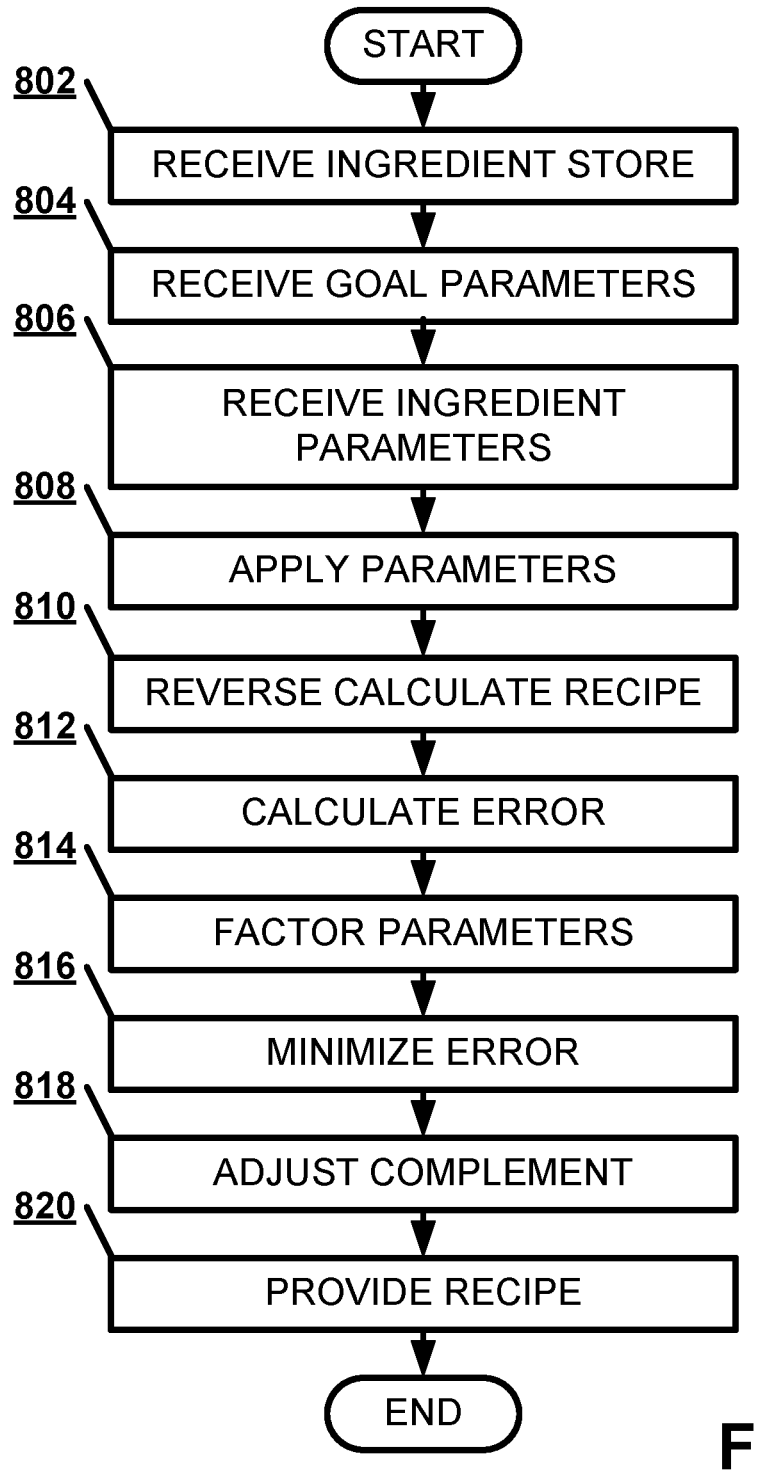
FIG. 8 illustrates, in a flowchart, one example of a method for generating a glaze recipe.

FIG. 8 illustrates, in a flowchart, one example of a method 800 for generating a glaze recipe. The solver engine may receive an ingredient store describing a set of ingredients available for mixing into a glaze slurry (Block 802). The solver engine may receive a goal parameter set describing a ceramic glaze (Block 804). The solver engine may receive an ingredient parameter set describing a recipe ingredient set used to create a glaze slurry (Block 806). The solver engine may apply the goal parameter set and the ingredient parameter set to a glaze process model to reflect user preferences for a goal chemical composition of the ceramic glaze (Block 808).

The solver engine may automatically reverse calculate a glaze recipe describing a recipe ingredient set to produce the ceramic glaze having a goal chemical description or a goal property description of the goal parameter set (Block 810). The solver engine may calculate an error value for a resulting chemical composition in comparison to a goal chemical composition for the ceramic glaze (Block 812). Thus, if the solver engine fails to find a glaze recipe producing an exact match, the solver engine may reverse calculate a glaze recipe producing an approximation of the goal chemical composition, possibly prioritizing the closest possible approximation. The solver engine may factor the goal parameter set and the ingredient parameter set into calculating the error value (Block 814). The solver engine may minimize the error value by adjusting the glaze recipe (Block 816). The solver engine may adjust a complementary chemical component of the chemical composition of the ceramic glaze in response to a chemical component adjustment of a chemical component of the goal chemical composition of the ceramic glaze (Block 818). The solver engine may provide a recipe ingredient set to produce the ceramic glaze (Block 820).

Figure 9:
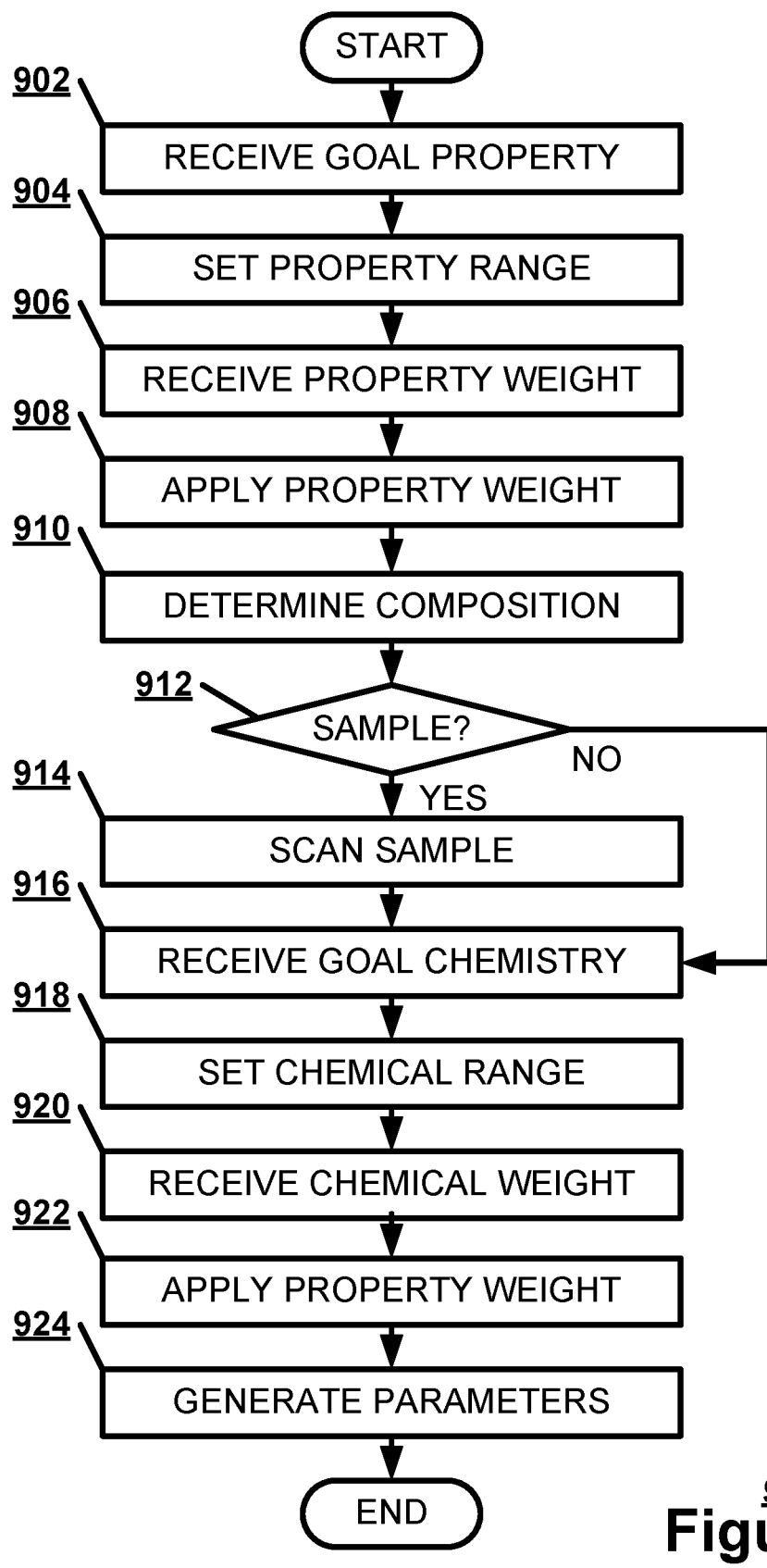
FIG. 9 illustrates, in a flowchart, one example of a method for generating a set of product parameters.

FIG. 9 illustrates, in a flowchart, one example of a method 900 for generating a set of product parameters. The solver engine may receive a goal property description for the ceramic glaze (Block 902). The solver engine may set a goal property range for a goal property description of the ceramic glaze (Block 904). The solver engine may receive a goal property weight for the goal property description of the ceramic glaze (Block 906). The solver engine may apply a goal property weight to a goal property description of the ceramic glaze (Block 908). The solver engine may determine the goal chemical composition for the ceramic glaze based on a goal property description (Block 910).

If the ceramic technician has a glaze sample of the desired finished glaze (Block 912), an assay device may scan a glaze sample to determine the goal chemical composition for the ceramic glaze (Block 914). The solver engine may receive a goal chemical composition for the ceramic glaze (Block 916). The solver engine may set a goal chemical range for a goal chemical component of the goal chemical composition of the ceramic glaze (Block 918). The solver engine may receive a goal component weight for the goal chemical component (Block 920). The solver engine may apply the goal component weight to the goal chemical component of the ceramic glaze (Block 922). The solver engine may generate a goal parameter set for the ceramic glaze (Block 924).

Figure 10:
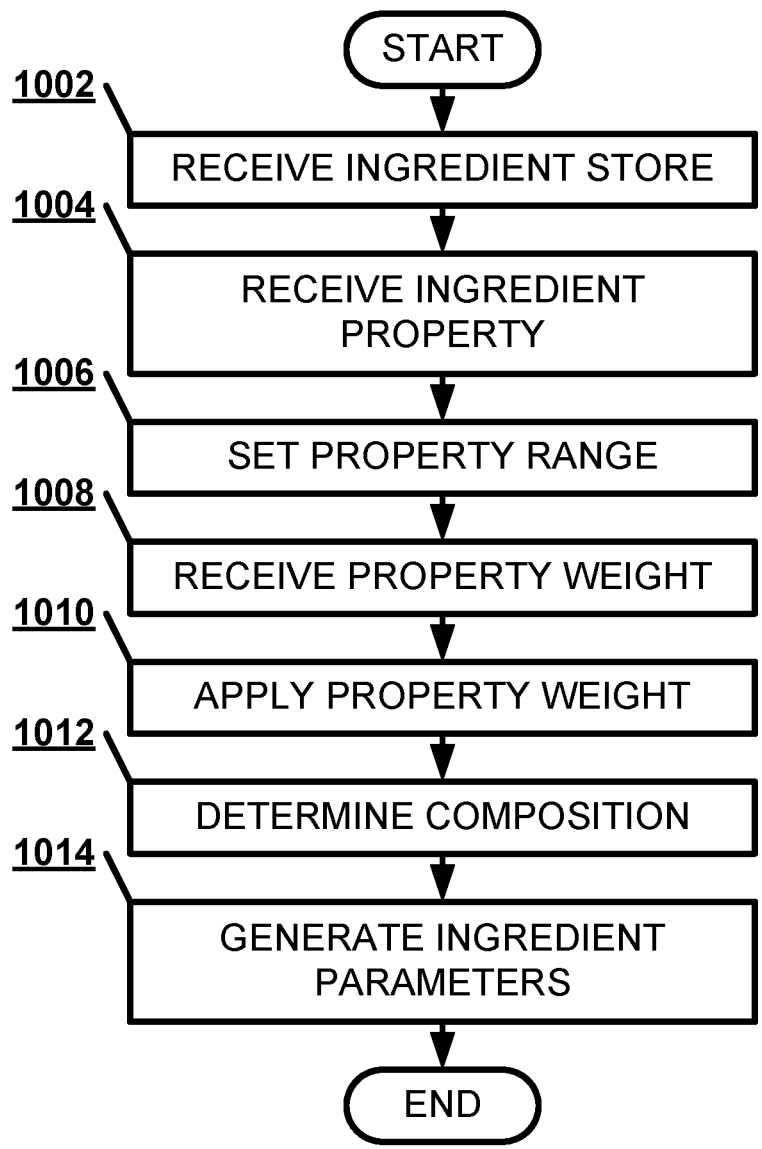
FIG. 10 illustrates, in a flowchart, one example of a method for generating a set of ingredient parameters.

FIG. 10 illustrates, in a flowchart, one example of a method 1000 for generating a set of ingredient parameters. The solver engine may receive an ingredient store describing a set of ingredients available for mixing into a glaze slurry (Block 1002). The solver engine may receive an ingredient property description for a recipe ingredient of the recipe ingredient set (Block 1004). The solver engine may set an ingredient range for a recipe ingredient of the recipe ingredient set (Block 1006). The solver engine may receive an ingredient property weight for a recipe ingredient of the recipe ingredient set (Block 1008). The solver engine may apply an ingredient property weight to a recipe ingredient of the recipe ingredient set (Block 1010). The solver engine may determine the ingredient chemical composition for the recipe ingredient set (Block 1012). The solver engine may generate an ingredient parameter set for the recipe ingredient set (Block 1014).

Although the subject matter has been described in language specific to structural features and/or methodological acts, it is to be understood that the subject matter in the appended claims is not necessarily limited to the specific features or acts described above. Rather, the specific features and acts described above are disclosed as example forms for implementing the claims.

Examples within the scope of the present invention may also include computer-readable storage media for carrying or having computer-executable instructions or data structures stored thereon. Such computer-readable storage media may be any available media that can be accessed by a general purpose or special purpose computer. By way of example, and not limitation, such computer-readable storage media can comprise RAM, ROM, EEPROM, CD-ROM or other optical disk storage, magnetic disk storage or other magnetic data storages, or any other medium which can be used to store desired program code means in the form of computer-executable instructions or data structures, as opposed to propagating media such as a signal or carrier wave. Computer-readable storage media explicitly does not refer to such propagating media. Combinations of the above should also be included within the scope of the computer-readable storage media.

Examples may also be practiced in distributed computing environments where tasks are performed by local and remote processing devices that are linked (either by hardwired links, wireless links, or by a combination thereof) through a communications network.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, objects, components, and data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Although the above description may contain specific details, they should not be construed as limiting the claims in any way. Other configurations of the described examples are part of the scope of the disclosure. For example, the principles of the disclosure may be applied to each individual user where each user may individually deploy such a system. This enables each user to utilize the benefits of the disclosure even if any one of a large number of possible applications do not use the functionality described herein. Multiple instances of electronic devices each may process the content in various possible ways. Implementations are not necessarily in one system used by all end users. Accordingly, the appended claims and their legal equivalents should only define the invention, rather than any specific examples given.

We claim:

1. A solver engine for a glazing system, comprising:
a descriptor interface configured to receive a goal descriptor describing a ceramic glaze;
a model applicator configured to apply a glaze process model to the goal descriptor to calculate the chemical composition of the ceramic glaze and to automatically reverse calculate a glaze recipe describing a recipe ingredient set to produce the chemical composition described by the goal descriptor; and
a glaze mixing machine interface configured to direct a glaze mixing machine to mix the recipe ingredient set to produce the ceramic glaze for application to a ceramic and firing in a kiln.

2. The solver engine of claim 1, further comprising:
an assay device interface configured to receive from an assay device a scan of a glaze sample to determine a goal chemical composition to act as the goal descriptor for the ceramic glaze.

3. The solver engine of claim 1, further comprising:
a user input configured to receive a goal chemical composition to act as the goal descriptor for the ceramic glaze.

4. The solver engine of claim 1, further comprising:
a user input configured to receive a goal property description to act as the goal descriptor for the ceramic glaze.

5. The solver engine of claim 1, wherein the model applicator is further configured to determine a goal chemical composition for the ceramic glaze based on a goal property description.

6. The solver engine of claim 1, wherein the model applicator is further configured to apply a goal property importance to a goal property description of the ceramic glaze.

7. The solver engine of claim 1, further comprising:
a model generator configured to set a goal property range for a goal property description of the ceramic glaze.

8. The solver engine of claim 1, further comprising:
a user input configured to receive an ingredient property description for a recipe ingredient of the recipe ingredient set.

9. The solver engine of claim 1, wherein the model applicator is further configured to apply an ingredient property importance to a recipe ingredient of the recipe ingredient set.

10. The solver engine of claim 1, further comprising:
a user input configured to receive an ingredient range for a recipe ingredient of the recipe ingredient set.

11. The solver engine of claim 1, further comprising:
a user input configured to receive a chemical component adjustment to a chemical component of the goal chemical composition of the ceramic glaze.

12. The solver engine of claim 1, wherein the model applicator is further configured to adjust a complementary chemical component of a goal chemical composition of the ceramic glaze in response to a chemical component adjustment of a chemical component of the goal chemical composition of the ceramic glaze.

13. The solver engine of claim 1, further comprising:
an assay device interface configured to receive from an assay device a scan of a resulting ceramic glaze of the glaze recipe.

14. The solver engine of claim 1, wherein a model applicator is further configured to adjust the glaze recipe in response to a scan of a resulting ceramic glaze of the glaze recipe.

15. A computing device, having a memory to store a series of instructions that are executed by at least one processor to implement the solver engine of claim 1, the computing device configured to
receive the goal descriptor describing the ceramic glaze;
apply the glaze process model to the goal descriptor;
calculate the chemical composition of the ceramic glaze;
automatically reverse calculate the glaze recipe describing the recipe ingredient set to produce the chemical composition described by the goal descriptor; and
direct the glaze mixing machine to mix the recipe ingredient set to produce the ceramic glaze for application to a ceramic and firing in a kiln.

16. The computing device of claim 15, wherein the computing device is further configured to
present the glaze recipe describing the recipe ingredient set to produce the ceramic glaze to a ceramic technician.

17. The computing device of claim 15, wherein the computing device is further configured to
calculate an error value for a resulting chemical composition set in comparison to a goal chemical composition for the ceramic glaze.

18. The computing device of claim 15, wherein the computing device is further configured to
adjust a complementary chemical component of the goal chemical composition of the ceramic glaze in response to a chemical component adjustment of a chemical component of the goal chemical composition of the ceramic glaze.

19. A machine-implemented method to implement the solver engine claim 1, comprising:
receiving the goal descriptor describing a ceramic glaze;
applying the glaze process model to the goal descriptor;
calculating the chemical composition of the ceramic glaze;
automatically reversing calculate a glaze recipe describing the recipe ingredient set to produce the chemical composition described by the goal descriptor; and
directing the glaze mixing machine to mix the recipe ingredient set to produce the ceramic glaze for application to a ceramic and firing in a kiln.

20. The method of claim 19, further comprising:
adjusting the glaze recipe in response to a scan of a resulting ceramic glaze of the glaze recipe.

* * * * *